United States Patent [19]
Budolfsen et al.

[11] Patent Number: 6,036,981
[45] Date of Patent: Mar. 14, 2000

[54] PROCESS FOR THE IMPROVEMENT OF GEL FORMATION OR VISCOSITY INCREASE

[75] Inventors: Gitte Budolfsen, Frederiksberg; Hans Peter Heldt-Hansen, Virum, both of Denmark

[73] Assignee: Novo Nordisk A/S, Bagsvaerd, Denmark

[21] Appl. No.: 09/034,668

[22] Filed: Mar. 4, 1998

Related U.S. Application Data

[63] Continuation of application No. PCT/DK96/00391, Sep. 17, 1996.

[30] Foreign Application Priority Data

Sep. 22, 1995 [DK] Denmark .................................. 1061/95

[51] Int. Cl.$^7$ ...................................................... A23B 7/10
[52] U.S. Cl. ................................ 426/49; 426/50; 426/51; 426/52
[58] Field of Search ................................ 426/49, 50, 51, 426/52

[56] References Cited

FOREIGN PATENT DOCUMENTS

WO 94/12055  6/1994  WIPO .

OTHER PUBLICATIONS

Flores et al, AN 85(03):H0053 FSTA, abstracting Flussiges Obst, 51 (7) 320–324 and 327–328, 1984.
Bock et al, AN 72(02):J0211 FSTA, abstracting Ernahrungsforschung, 15(4) 403–415, 1970.
Grampp, E., AN 73(02):J0297 FSTA, abstracting Dechema–Monographien, 70, 175–186, 1972.
Grampp, E., AN 77:112664 CA, abstracting Dechema–Monogr., 70, 175–186, 1972.
Chesson et al., "The Maceration of Vegetable Tissue By A Strain of *Bacillus Subtilis*". Jour. of Applied Bacteriology, 1978, 44, pp. 347–364.
Calesnick et al., "Propteries of a Commercial Fungal Pectase Eastern Regional Research Laboratory, Philadelphia, Pa., Aug. 9, 1950, Preparation", pp. 432–440.

*Primary Examiner*—Leslie Wong
*Attorney, Agent, or Firm*—Steve T. Zelson, Esq.; Reza Green, Esq.

[57] ABSTRACT

A process for increasing the viscosity or gel strength of certain food products is disclosed. By the process a pectinaceous homogenate or slurry is subjected to: a) a treatment with a mixture of enzymes, comprising one or more among galactanases, arabinanases, α-arabinofuranosidases, rhamnogalacturonan acetyl esterases (RGAE), endoglucanases, mannanases, xylanases, and proteolytic enzymes; b) a treatnent with a pectinesterase (PE), which PE is essentially free from pectic depolymerizing enzymes; followed by c) an enzyme inactivating treatment; said process being performed in the presence of divalent metal ions, especially $Ca^{2+}$, said ions being inherently present in said homogenate or slurry, or said ions being added at any time prior to, during or after the process steps (a) to (c). The final product may be a jam, marmalade, jelly, juice, paste, soup, dressing, sauce, condiment, ketchup, salsa, chutney, pudding, mousse, or other dessert.

23 Claims, No Drawings

PROCESS FOR THE IMPROVEMENT OF GEL FORMATION OR VISCOSITY INCREASE

CROSS-REFERENCE TO RELATED APPLICATIONS

This application is a continuation of PCT/DK96/00391 filed on Sep. 17, 1996, which claims priority under 35 U.S.C. 119 of Danish application serial no. 1061/95 filed Sep. 22, 1995.

FIELD OF THE INVENTION

The present invention relates to a process in which the well known effect of pectinesterase (EC 3.1.1.11, *"Enzyme Nomenclature* 19921" Academic Press, Inc., 1992) on the texture (viscosity increase/gel formation) of food products prepared from pectinaceous fruits and vegetables is improved by means of other specific carbohydrases belonging to the groups of cellulytic, hemicellulytic, pectinolytic, and proteolytic enzymes.

BACKGROUND OF THE INVENTION

A range of extracted plant derived hydrocolloids are traditionally used as texturizing agents for various food products. However, many food products, such as fruits and vegetables in themselves contain hydrocolloids, i.e. the plant cell wall material. With the aim of improving, in situ, viscosity and gelling capacity, a further enzymatic modification of the plant cell wall material per se is now proposed as a texturizing process.

The plant cell wall has a very complex nature consisting of different polysaccharides, small amounts of glycoproteins and phenolic compounds. The polysaccharides are traditionally divided into cellulose compounds, hemicellulose and pectic compounds.

The primary cell wall of most flowering plants are of the type I cell wall. In a type I cell wall the cellulose microfibrils are interlaced with xyloglucan polymers (approx. 50% of the total mass). The cellulose-xyloglucan framework is embedded in a matrix of pectic polysaccharides. The pectic matrix consists of smooth regions of polygalacturonic acids and of rhamnogalacturonan. The polygalacturonic acid areas are usually highly esterified by methoxyl groups, acetylation of the hydroxy groups also occurs. Side groups consisting of araban, galactan and arabinogalactan are attached to the rhamnogalacturonan residues. The pectic polysaccharides constitute approx. 30° C. of the total mass. Mannans, β-(1-3)-glucans and arabinoxylans also play a role as pectic-interlocking agents. The cell wall further consists of structural proteins, of which extensin is thought to play the major role. (Carpita, N. C. and Gibeaut, D. M., 1993, *Plant Journal* 3 (1), 1–30, Keegstra, K. et al, 1973, Plant *Physiol.*, 51, 188–196).

The endogenous, highly methoxylated content of pectin (HM pectin) in various fruits and vegetables can enzymatically be modified to a low methoxylated pectin (LM pectin) by pectinesterase (PE)(EC 3.1.1.11). In combination with the natural content or further addition of calcium ions this is sufficient for an in situ gelation or an in situ thickening to take place (Calesnik, E. J. et al 1950, *Arch. of Biochem.*, 29, 432–440. Meurens, M., 1978, *Rev. Ferment. Ind. Aliment.*, 33, 95–104). These authors also indicate that use of a PE preparation purified is for pectic depolymerizing enzymes, such as polygalacturonases, would allow the gelation to take place by utilising the endogenous pectin in situ.

Such a process is furthermore described in International patent application no. PCT/EP93/03379 (Gist-Brocades NV), where also the use of a PE substantially free from pectic depolymerizing enzymes is described for the gelling of food products.

However, these methods still leave room for improving the properties of such food products.

It is thus the object of this invention to provide a method for increasing the viscosity or gel strength in a pectinaceous mass.

SUMMARY OF THE INVENTION

The present invention relates to a process for the treatment of a pectinaceous homogenate or slurry, wherein said homogenate or slurry is subjected to:

a) a treatment with a mixture of enzymes, comprising one or more among galactanases, arabinanases, α-arabinofuranosidases, rhamnogalacturonan acetyl esterases (RGAE), endoglucanases, mannanases, xylanases, and proteolytic enzymes, b) a treatment with a pectinesterase (PE), which PE is essentially free from pectic depolymerizing enzymes, followed by c) an enzyme inactivating treatment, said process being performed in the presence of divalent metal ions, especially $Ca^{2+}$, said ions being inherently present in said homogenate or slurry, or said ions being added at any time prior to, during or after the process steps (a) to (c).

The invention furthermore relates to a mixture of enzymes comprising one or more among galactanases, arabinanases, α-arabinofuranosidases, rhamnogalacturonan acetyl esterases (RGAE), endoglucanases, mannanases, xylanases, and proteolytic enzymes, which mixture is substantially free from pectic depolymerizing enzymes.

The invention in a third aspect relates to the use of such is a mixture for the treatment of a pectinaceous homogenate or slurry in combination with a concurrent or sequential treatment with a PE.

Lastly the invention relates to a product produced by the method of the first aspect of the invention.

DETAILED DESCRIPTION OF THE INVENTION

As indicated the present invention relates to a process for the treatment of a pectinaceous homogenate or slurry, wherein said homogenate or slurry is subjected to:

a) a treatment with a mixture of enzymes, comprising one or more among galactanases, arabinanases, α-arabinofuranosidases, rhamnogalacturonan acetyl esterases (RGAE), endoglucanases, mannanases, xylanases, and proteolytic enzymes, b) a treatment with a pectinesterase (PE), which PE is essentially free from pectic depolymerizing enzymes, followed by c) an enzyme inactivating treatment, said process being performed in the presence of divalent metal ions, especially $Ca^{2+}$, said ions being inherently present in said homogenate or slurry, or said ions being added at any time prior to, during or after the process steps (a) to (c).

Cellulytic and hemicellulytic enzymes, such as xylanases, endoglucanases, and mannanases have the ability to loosen the pectic material and presumably to make it more susceptible to the action of specific pectinolytic enzymes. Pectinolytic enzymes, such as galactanases, arabinanases, α-arabinofuranosidases, and rhamnogalacturonan acetyl esterases (RGAE) can be used for a sort of debranching of the pectic polysaccharides.

Proteolytic enzymes, such as proteases may as well show an impact on the availability of pectin. Such proteases may be acid proteases, alkaline proteases, highly alkaline proteases and metallo-proteases.

More specific definitions of the above enzymes can be found in "Enzyme Nomenclature 1992" Academic Press, Inc., 1992.

The concerted action of selected cellulytic, hemicellulytic, pectinolytic, and proteolytic enzymes added prior to, or simultaneous with in situ gelation of pectinaceous fruits and vegetables by PE has proven to increase the gel strength or the viscosity of fruit/vegetable products.

The debranching of the pectin molecules may also in certain cases introduce a viscosity increase as explained below. It is well known from the literature that the structure of the polymer is of importance in determining the functional properties.

Linear polysaccharides of the same molecular weight as that of a branched polysaccharide will show higher viscosity, as the linear polymer can gyrate, causing the molecule to sweep through large volumes of space. Therefore the linear molecules will come into contact with each other more easily, and increase the friction or the viscosity characteristics of the solution at much lower concentrations than will highly branched molecules (c.f. Glicksman M., 1982, *Food Hydrocolloids* 1, 4–10)

Further, the acetyl groups of the hairy regions may be partially removed by rhamnogalacturonan acetyl esterase. This will improve the hydrophilicity and thus change the resistance to shearing. Glicksman (supra) discusses these aspects and mentions that the charge of a linear polymer is of importance for its stabilising effect.

According to an embodiment of the invention the process may be performed by treating the material with the PE and the mixzure of enzymes simultaneously, or, according to further embodiments the treatments may be performed sequentially with the PE treatment either prior to or after the treatment with the enzyme mixture.

According to a further embodiment the enzyme inactivation step may be performed after each of the treatments mentioned above.

The process of the invention may be performed on pectinaceous homogenates or slurries comprising plant parts, and/or material of animal origin.

The plant parts are normally selected from fruits and vegetables, especially such as apples, tomatoes, oranges, lemons, grapes, lime, pears, berries, such as blackcurrant, strawberries, carrots, and peas.

The homogenate or slurry will often be selected among is juice, puree, concentrate, ketchup, condiment, sauce, soup, salsa, chutney, yoghurt, and deserts.

According to the invention the method will be carried out at appropriate conditions, for which some parameters may be mentioned, such as that treatment (a) is performed at a temperature from 10° C. to 60° C., preferably from 30° C. to 50° C., a pH from 2 to 7, preferably from 3 to 5, and for a time from 2 to 120 minutes, preferably from 30 to 60 minutes; treatment (b) is performed at a temperature from 5° C. to 50° C., preferably from 20° C. to 40° C., a pH from 2 to 7, preferably from 3 to 5, and for a time from 2 to 120 minutes, preferably from 30 to 60 minutes; and treatment (c) is a heat inactivation, preferably performed at a temperature from 80° C. to 100° C., preferably 85° C. and 90° C. for a time from 10 seconds to 600 seconds.

If the two treatments are performed simultaneously the following conditions may be employed, whereby the process is performed at a temperature from 10° C. to 50° C., preferably from 30° C. to 40° C., a pH from 2 to 7, preferably from 3 to 5, and for a time from 2 to 120 minutes, preferably from 30 to 60 minutes.

In the process of the invention the enzyme mixture will normally be applied in an amount from 5 to 150, preferably from 7 to 100, and better from 10 to 50 mg enzyme protein per kg homogenate or slurry for each of the enzymes. For a xylanase the amount in FXU (Farvet Xylan Unit) will be from 150 to 4000, preferably from 225 to 3000, and better from 300 to 1500 FXU per kg homogenate or slurry.

The activity of the xylanase is indicated in FXU, the measurement of which is described in the Materials and Methods section below.

In the process of the invention the PE will normally be applied in an amount from 2 to 60, preferably from 5 to 40, and better from 10 to 25 PEU per kg homogenate or slurry.

The activity of the pectinesterase is indicated in Pectin Esterase Units (PEU) defined as the amount of enzyme which under standardised conditions hydrolyses 1 mmol carboxyl groups per minute. A folder describing the Novo Nordisk assay ABT-SM-0005.02.1 is available upon request.

According to an embodiment of the invention the mixture of enzymes and the PE is applied in a ratio from 1:10 to 50:1, preferably from 1:2 to 5:1, whereby the amounts of both components are on a weight of protein measure.

The invention further relates to a mixture of enzymes comprising one or more among galactanases, arabinanases, α-arabinofuranosidases, rhamnogalacturonan acetyl esterases (RGAE), endoglucanases, mannanases, xylanases, and proteolytic enzymes, especially proteases.

Such enzymes are available in purified form from different sources. Procedures for obtaining these are i.a. described in (galactanase) WO 92/13945, (arabinases) WO 94/20611, (RGAE) WO 93/20190, (endo-glucanases) WO 93/20193, (endo-glucanases) WO 94/14950, (mannanase) WO 94/25576, (xylanases) WO 94/21785, (proteases) WO 95/02044.

The PE used in the invention is derived from a fungus of the genus Aspergillus, preferably *A. japonicus*, (S. Ishii et al., 1979, *Journal of Food Science* 44, p 611–614), A. aculeatus, A. niger (EP 0 388 593 A1), A. awamori (EP 0 388 593 A1), or the genera Fusarium, Sclerotonia, or Penicillium, (Kikkoman: DE 2843351; U.S. Pat. No. 4,200, 694). These pectinesterases exhibit a relatively low pH optimum, corresponding to the relatively low pH optimum of many fruits.

In a preferred embodiment the pectinesterase is an enzyme preparation substantially free from pectin depolymerizing enzymes. Such enzymes are obtainable by using a host system for the expression of the enzyme which does not produce any pectin s depolymerizing enzymes (WO 94/25575) now U.S. Pat. No. 5,707,847.

The invention also relates to the use of a mixture as defined above for the treatment of a pectinaceous homogenate or slurry.

Furthermore the invention relates to a gel produced by the method of the invention.

Such a gel may be a jam, marmalade, jelly, juice, paste, soup, dressing, sauce, condiment, ketchup, salsa, chutney, pudding, mousse, or other desert.

MATERIALS AND METHODS
Oranges
Broccoli
Hot break tomato paste

Meat Mincer (knife: 2 mm holes)
Fryma Mill
Brookfield Viscometer, DVII
Blotter test paper (Bridge & Company)
Enzymes: PE, RGAE, galactanase, arabinanase, α-arabinofuranosidase, endo glucanase III, protease II. The production of these enzymes are indicated in: (galactanase) WO 92/13945, (arabinases) WO 94/20611, (RGAE) WO 93/20190, (endo-glucanase I) WO 93/20193, (endo-glucanase II, IV) WO 94/14950, (mannanase) WO 94/25576, (xylanase I, II, III) WO 94/21785, (protease II) WO 95/02044, and (PE) WO 94/25575.

Xylanolytic Activity

The xylanolytic activity can be expressed in FXU-units, determined at pH 6.0 with remazol-xylan (4-O-methyl-D-glucurono-D-xylan dyed with Remazol Brilliant Blue R, Fluka) as substrate.

A xylanase sample is incubated with the remazol-xylan substrate. The background of non-degraded dyed substrate is precipitated by ethanol. The remaining blue colour in the supernatant (as determined spectrophotometrically at 585 nm) is proportional to the xylanase activity, and the xylanase units are then determined relatively to an enzyme standard at standard reaction conditions, i.e. at 50.0°°C., pH 6.0, and 30 minutes reaction time.

A folder AF 293.6/1 describing this analytical method in more detail is available upon request to Novo Nordisk A/S, Denmark, which folder is hereby included by reference.
SMS Texture Analyser TA-XT2 (Stable Micro Systems, XT.RA Dimensions, Operating Manual version 37)

Texture Analysis:

The gel strength/hardness of the slurries was measured by the Texture Analyzer by compression analysis. The compression was carried out by using a flat cylinder, f 20 mm and with a speed of 2.0 mm/s. The compression make up a total of 20% of the sample height. From the record of the force-time curve the gel strength measured as the peak force, is directly obtained. The gel strength was measured as an average of four measurements and is given in N.

Viscosity Measurements:

The viscosity was measured by Spindel C, specification no. 93. Measurements at shear rate 2.5 rpm and 20 rpm were carried out.

EXAMPLES

Example 1

Fresh oranges were washed and then chopped in a meat mincer. The oranges were further homogenised by using a Fryma Mill. Tap water was added: 6 part of oranges and 4 parts of tap water. Then the slurry was heat treated by steam injection at 100° C. for 2 min at 1 atm. Four samples of 200 g of the slurry were now adjusted to 40° C. and added enzymes as follows:

Sample No. 1): Control, heat inactivated enzyme mixture (enzyme mixture corresponding to sample 4.

Sample No. 2): PE 10.5 PEU/kg slurry

Sample No. 3): RGAE, galactanase, arabinanase, α-arabinofuranosidase, endo glucanase III, protease II, 25 mg/kg slurry of each of the enzymes.

Sample No. 4): PE 10.5 PEU/kg slurry, RGAE, galactanase, arabinanase, α-arabinofuranosidase, endo glucanase III, protease II, 25 mg/kg slurry of each.

The slurries were allowed to stand for 1 hour at 40 C and were finally heat inactivated at 85° C. for 3 min in a microwave oven. 4×50 g of each of the samples were then poured into 100 is ml beakers, sealed and placed in the refrigerator until the next day. The gel strength of the samples was measured by texture analysis as described in "Materials and Methods".

The results appear from Table I below:

TABLE I

| Sample No. | 1, Control | 2, PE | 3, Mix | 4, PE + Mix |
|---|---|---|---|---|
| Gel strength N | 0.1 | 2.1 | 0.1 | 5.6 |

It is clearly seen that the debranching of the pectin chain and the possible liberation of intact pectin improves the gel strength of the products, when using both PE and the mix, whereas the use of the mixture alone does not provide any increase in gel strength, and the use of PE alone gives the expected improvement in gel strength.

Example 2

Fresh broccoli was washed and chopped into smaller pieces. Water was added 1:1 and then the vegetables was cooked for 15 min. The mixture was then chopped in a meat mincer (2 mm holes). Four samples of 200 g were adjusted to 40° C. and added enzymes as follows:

Sample No. 1): Control, heat inactivated enzyme mixture ((enzyme mixture corresponding to sample 4)

Sample No. 2): PE 10.5 PEU/kg slurry

Sample No. 3): RGAE, galactanase, arabinanase, α-arabinofuranosidase, endo glucanase III, protease II, 25 mg/kg slurry of each of the enzymes.

Sample No. 4): PE 10.5 PEU/kg slurry, RGAE, galactanase, arabinanase, a-arabinofuranosidase, endo glucanase III, protease II, 25 mg/kg slurry of each.

The slurries were allowed to stand for 1 hour at 40° C. and is were finally heat inactivated at 85° C. for 3 min in a microwave oven. 4×50 g of each of the samples were poured into 100 ml beakers, sealed and placed in the refrigerator until the next day. The gel strength of the samples was measured by texture analysis as described above (Materials and Methods). The results appears from Table II.

TABLE II

| Sample No. | 1, Control | 2, PE | 3, Mixture | 4, PE + Mix |
|---|---|---|---|---|
| Gel strength, N | 0.9 | 1.2 | 0.9 | 1.5 |

The results are similar to those of Example 1, and it is clearly seen that the debranching of the pectin chain and the possible liberation of intact pectin improves the gel strength of the products.

Example 3

Hot break tomato paste was diluted from 23% soluble solids to 8.5% soluble solids and homogenised in a homogeniser at 300 bar. Afterwards samples of 455 g were weighed out in 1000 ml containelrs, the temperature was adjusted to 40° C.

Enzyme Preparation:

Ten portions of 455 g substrate were prepared and added enzyme as follows:

1) PE, 10.5 PEU/kg undiluted paste

2) Xylanase II, 810 FXU/kg undiluted caste

3) Xylanase I, 810 FXU/kg undiluted paste
4) Arabinanase, 25 mg/g undiluted paste
5) Alpha-arabinanase, 25 mg/kg undiluted paste
6) PE, 10.5 PEU/kg undiluted paste+Xylanase II, 810 FXU/kg undiluted paste
7) PE, 10.5 PEU/kg undiluted paste+Xylanase I, 810 FXU/kg undiluted paste
8) PE, 10.5 PEU/kg undiluted paste+Arabinanase, 25 mg/kg undiluted paste
9) PE, 10.5 PEU/kg undiluted paste+Alpha-arabinanase, 25 mg/kg undiluted paste
10) Control with no enzyme addition (The enzymes were added in final volumes of 25 ml to each of the 455 g portions)

The samples were incubated for 30 min at 40° C.

Preparation of Substrate for Analysis:

After the enzyme treatment a ketchup was prepared by adding 300 g of brine. The brine consist of sugar, salt and acetic acid (Skott, W. P. *Die Industrielle Obst- und Gemüseverwertung*, 1970 55 229–234). The prepared ketchups were then heat treated, 88° C. in 3 min. The ketchup samples were then distributed and cooled in an ice bath and finally placed in the refrigerator until analysis could take place.

The results appears from Table III.

TABLE III

| | Viscosity 2.5 rpm cP | Viscosity 20 rpm cP |
|---|---|---|
| 1) PE | 10670 | 2050 |
| 2) Xylanase II | 9425 | 1695 |
| 3) Xylanase I | 9365 | 1765 |
| 4) Arabinanase | 9355 | 1645 |
| 5) α-arabinofuranosidase | 9980 | 1745 |
| 6) PE + Xylanase II | 12090 | 2340 |
| 7) PE + Xylanase I | 12610 | 2375 |
| 8) PE, + Arabinanase | 11485 | 2150 |
| 9) PE + α-arabinofuranosidase | 11265 | 2240 |
| 10) Control (no enzymes) | 9465 | 1690 |

Compared to the control the PE addition alone results in a pronounced viscosity increase. Samples Nos 2–5 however, do not result in a viscosity increase compared to the control and neither compared to the PE sample (No 1). Surprisingly, however, it is observed that the concerted action of PE and Xylanase I, Xylanase II, Arabinanase and a-arabinofuranosidase, respectively results in improved levels of viscosity at both shear rates compared to PE. It is thus concluded that a synergistic effect has been obtained (sample Nos 6–9)

We claim:

1. A process for preparing a food product, said process comprising
   (i) treating a pectinaceous homogenate or slurry with
      a) one or more enzymes selected from the group consisting of cellulytic, hemi-cellulytic, pectinolytic and proteolytic enzymes, wherein said enzymes do not include pectin depolymerizing enzymes; and
      b) a pectinesterase (PE), wherein said enzymes are essentially free from pectic depolymerizing activity; and
   (ii) subjecting said treated homogenate or slurry to an enzyme inactivating treatment,
wherein said treated homogenate or slurry is capable of forming a gel having an increased gel strength or exhibits an increased viscosity relative to an untreated homogenate or slurry or to a homogenate or slurry treated only with the enzymes of (a) or (b).

2. A process for increasing the viscosity and/or gel-forming capability of a pectinaceous homogenate or slurry, said process comprising
   (i) treating said homogenate or slurry with
      (a) one or more enzymes selected from the group consisting of cellulytic, hemi-cellulytic, pectinolytic and proteolytic enzymes, wherein said enzymes do not include pectin depolymerizing enzymes; and
      b) a pectinesterase (PE), wherein said enzymes are essentially free from pectic depolymerizing activity, followed by
   (ii) subjecting said treated homogenate or slurry to an enzyme inactivating treatment,
wherein said treated homogenate or slurry is capable of forming a gel having an increased gel strength or exhibits an increased viscosity relative to an untreated homogenate or slurry or to a homogenate or slurry treated only with the enzymes of (a) or b.

3. The process of claim 1, wherein the one or more enzymes of step a) are selected from the group consisting of galactanases, arabinanases, B-arabinofuranosidases, rhamnogalacturonan acetyl esterases (RGAE), endoglucanases, mannanases, xylanases, and proteolytic enzymes.

4. The process of claim 1, wherein divalent metal ions are added at any time prior to, during or after the process steps (i)(a), (i)(b), or (ii).

5. The process of any of claim 1, wherein the divalent metal ions are $Ca^{2+}$.

6. The process of claim 1, wherein steps (i)(a) and (i)(b) are performed sequentially or simultaneously.

7. The process of claim 6, wherein an enzyme inactivating treatment is performed between steps (i)(a) and (i)(b).

8. The process of any of claim 1, wherein said pectinaceous homogenate or slurry comprises plant parts.

9. The process of claim 8, wherein said homogenate or slurry further comprises material of animal origin.

10. The process of any of claims 8, wherein said plant parts originate from fruits or vegetables.

11. The process of claim 10, wherein said fruits are selected from the group consisting of apples, tomatoes oranges, lemons, grapes, lime, pears, and berries, and said vegetables are selected from the group consisting of carrots, peas, tomatoes, broccoli, and cauliflower.

12. The process of claim 8, wherein said homogenate or slurry is selected from the group consisting of a juice, puree, concentrate, ketchup, condiment, sauce, soup, salsa, chutney, yoghurt, and a dessert.

13. The process of claim 1, wherein step (i)(a) is performed at a temperature from 10° C. to 60° C., at a pH from 2 to 7, and for a time from 2 to 120 minutes.

14. The process of claim 1, wherein step (i)(b) is performed at a temperature from 5° C. to 50° C., at a pH from 2 to 7, and for a time from 2 to 120 minutes.

15. The process of claim 6, wherein steps (i)(a) and (b) are performed simultaneously at a temperature from 10° C. to 50° C., at a pH from 2 to 7, and for a time from 2 to 120 minutes.

16. The process of claim 1, wherein said treatment (ii) is a heat inactivation.

17. The process of claim 7, wherein said enzyme inactivation after step (i)(a) is a heat inactivation.

18. The process of any of the claims 16, wherein the heat inactivation is performed at a temperature from 80° C. to 100° C. for a time from 10 seconds to 600 seconds.

19. The process of claim 16, wherein the heat inactivation is performed at a temperature from 85° C. to 90° C.

20. A product obtainable by a method according to claim 1.

21. The product of claim 20, which is a jam, marmalade, jelly, juice, paste, soup, dressing, sauce, condiment, ketchup, salsa, chutney, pudding, mousse, or dessert.

22. A process for preparing a food product, said process comprising
   (i) treating a pectinaceous homogenate or slurry with
      a) one or more enzymes selected from the group consisting of cellulytic, hemi-cellulytic, pectinolytic and proteolytic enzymes, wherein said enzymes do not include pectin depolymerizing enzymes; and
      b) a pectinesterase (PE), wherein said PE is produced in a recombinant cell which comprises heterologous PE-encoding DNA and which does not produce pectin-depolymerizing enzymes; and
   (ii) subjecting said treated homogenate or slurry to an enzyme inactivating treatment,
   wherein said treated homogenate or slurry is capable of forming a gel having an increased gel strength or exhibits an increased viscosity relative to an untreated homogenate or slurry or to a homogenate or slurry treated only with the enzymes of (a) or (b).

23. A process for increasing the viscosity and/or gel-forming capability of a pectinaceous homogenate or slurry, said process comprising
   (i) treating said homogenate or slurry with
      (a) one or more enzymes selected from the group consisting of cellulytic, hemi-cellulytic, pectinolytic and proteolytic enzymes, wherein said enzymes do not include pectin depolymerizing enzymes; and
      b) a pectinesterase (PE), wherein said PE is produced in a recombinant cell which comprises heterologous PE-encoding DNA and which does not produce pectin-depolymerizing enzymes, followed by
   (ii) subjecting said treated homogenate or slurry to an enzyme inactivating treatment,
   wherein said treated homogenate or slurry is capable of forming a gel having an increased gel strength or exhibits an increased viscosity relative to an untreated homogenate or slurry or to a homogenate or slurry treated only with the enzymes of (a) or (b).

* * * * *